(12) United States Patent
Tsutsumi

(10) Patent No.: US 6,841,716 B1
(45) Date of Patent: Jan. 11, 2005

(54) PATCH

(75) Inventor: Nobuo Tsutsumi, Tokyo (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/959,928

(22) PCT Filed: Apr. 27, 2000

(86) PCT No.: PCT/JP00/02791

§ 371 (c)(1),
(2), (4) Date: Nov. 13, 2001

(87) PCT Pub. No.: WO00/69422

PCT Pub. Date: Nov. 23, 2000

(30) Foreign Application Priority Data

May 13, 1999 (JP) ............................................. 11/133037

(51) Int. Cl.[7] ................................................ A61F 13/00
(52) U.S. Cl. ............................. 602/57; 602/42; 602/52
(58) Field of Search ...................... 602/41–59; 206/440, 206/441; 129/888, 889; D24/189; 604/304–308; 424/443–449

(56) References Cited

U.S. PATENT DOCUMENTS 5,419,913 A   5/1995   Podell et al.

FOREIGN PATENT DOCUMENTS

| EP | 0 354 315 | * | 2/1990 |
| EP | 0 788 784 A1 | | 8/1997 |
| EP | 0 882 460 A2 | | 12/1998 |
| GB | 2 148 125 A | | 5/1985 |
| JP | 58-124123 U | | 8/1983 |
| JP | 58-124123 | | 8/1983 |
| JP | 63-14530 U | | 1/1988 |
| JP | 63-14530 | | 1/1988 |
| JP | 1-165023 | | 11/1989 |
| JP | 1-165023 U | | 11/1989 |
| JP | 3-59327 | | 6/1991 |
| JP | 3-59327 U | | 6/1991 |
| JP | 4-57874 | | 2/1992 |
| JP | 7-38138 U | | 5/1995 |
| JP | 7-38138 | | 7/1995 |
| JP | 11-1432 | | 1/1999 |

* cited by examiner

Primary Examiner—Kim M. Lewis
(74) Attorney, Agent, or Firm—Fitch, Even, Tabin & Flannery

(57) ABSTRACT

According to the invention, a patch provided with a support 1, an adhesive layer 2 laminated on one side of the support, and a release film 4 attached in a releasable manner to the adhesive layer and having a slit 42 running from one edge to the opposite edge, is characterized in that the shape of the slit in the release film is a wave shape such that, by simply bending the support slightly along the slit while the exposed side of the adhesive layer which has been exposed by peeling off part of the release film along the slit is attached to the attachment site, the edge 44 of the slit of the remaining release film can promptly protrude outward from between the attachment site and the adhesive layer.

8 Claims, 5 Drawing Sheets

PATCH

This application is the National phase of International Application PCT/JP00/02791, filed 27 Apr. 2000, which designated the U.S., and was filed in other than the English language.

TECHNICAL FIELD

The present invention relates to a patch for a plaster or poultice, and more specifically it relates to a patch that can be easily attached to patch-sites.

BACKGROUND ART

Patches such as shown in FIG. 7 have been known in the prior art. Such patches comprise a patch body 30 composed of a roughly rectangular support 10 made of a nonwoven fabric or the like and an adhesive layer 20 laminated over its entirety, and a release film 40 which is attached to the adhesive layer in a releasable manner. The release film 40 is provided with a large wave-shaped slit 50 at approximately the center.

When this type of patch is used, because the release film 40 has a wave-shaped slit 50, the portion of the release film along the slit 50 separates from the adhesive layer 20 when the patch is bent, as shown in FIG. 7. A separated portion 60 (hereunder referred to as the "grip section") of the release film 40 is gripped with the fingers and used to peel off half of the release film 40. In order to make the release film 40 easier to grip with the fingers, the height H of the wave-shaped slit 50 has conventionally been approximately the size of the fingertip, or about 15 mm±2 mm. The exposed adhesive layer 20 is then attached to the patch site such as an affected area of the body, and finally the remaining half of the release film is peeled off while attaching the entire adhesive layer 20.

One of the requirements for conventional patches has been a property to prevent their peeling and falling off during use on areas of the body such as joints and their surrounding muscles which experience active movement that causes considerable stretching of the skin. A modification has therefore been devised whereby the support 10 is given flexibility and elasticity and the patch body 30 is made thinner to increase its flexibility and elasticity. On the other hand, release films 40 which are thin but have suitable rigidity have also been used in order to facilitate handling of more flexible patches and to allow easier release by utilizing the difference in softness with the support 10.

With the conventional patches such as shown in FIG. 7, however, when the adhesive layer 20 of the patch is attached to the affected area of the skin S and the remaining release film 40 is peeled off, as shown in FIGS. 8A and B, the grip section 60 sometimes gets caught between the skin S and the adhesive layer 20 and is difficult to grip with the finger.

In light of this problem of the prior art, it is an object of the present invention to provide a novel patch with a function allowing smooth attachment to patch sites such as affected areas of the skin.

DISCLOSURE OF THE INVENTION

As a result of much diligent research directed toward achieving the aforementioned object, the present inventors have found that the cause of this problem associated with patches having a large wave-shaped slit 50 in the release film 40 is as follows. As shown in FIG. 8A, a high height H of the wave-shaped slit 50 of the release film 40 provides sufficient area as the grip section 60 for release, but also increases the area of the adhesive section 70 which inhibits release, and since the support 10 is thin with high flexibility and elasticity, the cohesion between the inhibiting adhesive section 70 and the skin S is greater, such that the bend line R of the support 10 shifts toward the valley Y end instead of the hill X end of the wave-shaped slit, as shown in FIG. 8.

The present inventors have also found that in order to allow smooth attachment of the patch to the affected area of skin S, it is effective to appropriately reduce the height H of the wave-shape slit 50 of the release film 40, thereby shrinking the area of the grip section 60 during release.

The patch of the invention is based on this finding, and specifically, it is a patch provided with a support, an adhesive layer laminated on one side of the support, and a release film attached in a releasable manner to the adhesive layer and having a slit running from one edge to the opposite edge, the patch being characterized in that the shape of the slit in the release film is a wave shape such that, by simply bending the support slightly along the slit while the exposed side of the adhesive layer which has been exposed by peeling off part of the release film along the slit is attached to the attachment site, the edge of the slit of the remaining release film can promptly protrude outward without getting caught between the attachment site and the adhesive layer. The term "wave-shaped" as used herein will refer to sine wave-like waveforms as well as sawtooth waves.

Specifically, the wave-shaped slit preferably has a wave height of 4 mm to 8 mm. Here, the "wave height" is the value corresponding to the amplitude where the shape of the slit approximates a complete wave, and it is the height represented as "H" in FIG. 4 and FIG. 8.

By using a release film satisfying the above-mentioned condition, it is possible to easily grip the remaining portion of the release film with the fingers when peeling it off, without the grip section of the release film getting caught between the attachment site and the support.

The wave-shaped slit of the release film also preferably has a wave pitch of 6 mm to 12.5 mm. Here, the "wave pitch" is the value corresponding to the wavelength where the shape of the slit approximates a complete wave, and it is the height represented by "P" in FIG. 4.

By using a release film satisfying the above-mentioned condition, the grip section formed in the release film can be given an area of a size appropriate to permit protrusion outward from the attachment site and facilitate gripping with the fingers.

The patch of the invention may also have two wave-shaped slits in the release film, with the two slits substantially parallel to each other.

A release film satisfying this condition will allow the release film to be peeled off between the slits before attachment so that the exposed adhesive layer surface can be used as a paste area for provisional attachment to the attachment site. Since the patch is affixed to the attachment site, such as an affected area, this function allows attachment while easily peeling off the edge of the remaining release film, for a smoother series of attachment steps. Such provisional attachment also allows reattachment so that more precise attachment can be achieved to the desired site of the affected area.

When two wave-shaped slits are formed in the release film, a spacing between the slits of 20 mm to 30 mm is effective for the purpose of carrying out the function described above.

BEST MODE FOR CARRYING OUT THE INVENTION

Figure 1:
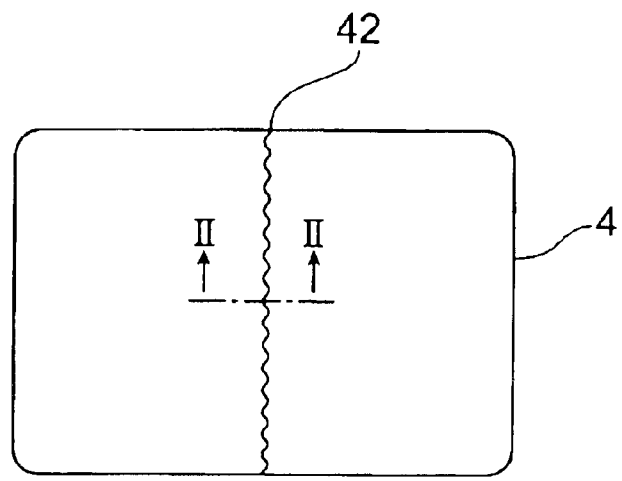
FIG. 1 is a plan view of a first embodiment of the patch of the invention.

Preferred embodiments of the invention will now be explained in detail with reference to the attached drawings. In the drawings, identical or corresponding members are indicated by like reference numerals.

Figure 2:
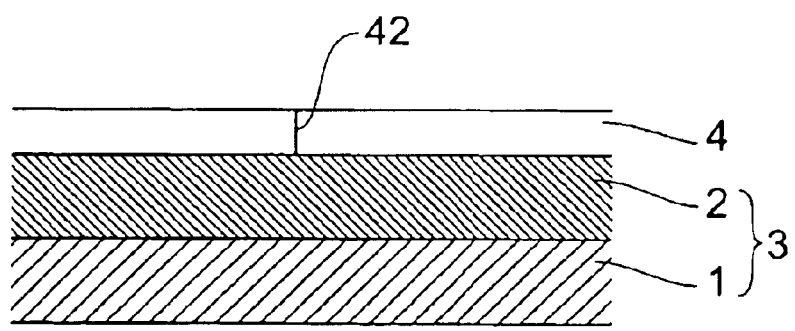
FIG. 2 is an expanded abbreviated cross-sectional view of the section along line II—II in FIG. 1.

FIG. 1 is a plan view of a first preferred embodiment of the patch of the invention, and FIG. 2 is an expanded abbreviated cross-sectional view along line II—II of FIG. 1.

As shown in FIG. 1 and FIG. 2, the patch of the invention has a construction with a patch body 3 comprising a roughly rectangular support 1 and an adhesive layer 2 laminated over approximately the entire surface of the support 1, and a release film 4 attached over approximately the entire surface of the adhesive layer 2 for release during use.

The structural material of the support 1 is not particularly restricted, but it is preferably a film, woven fabric, knitted fabric, nonwoven fabric or laminate thereof, composed of a synthetic resin such as polyethylene terephthalate (PET), ethylene-vinyl acetate copolymer (EVA), a block copolymer resin composed mainly of vinyl chloride, polyethylene, polybutadiene, styrene-butadiene or styrene-isoprene, butadiene-styrene-methyl methacrylate copolymer, or nylon, polyurethane, alkoxyalkyl (meth)acrylate copolymer, polyvinyl acetal, polyamide, rayon or the like.

The support 1 is preferably one with suitable flexibility and elasticity. The thickness of the support 1 is preferably 0.01 mm to 5 mm. A thickness of the support 1 of less than 0.01 mm tends to result in poor handling properties and tends to produce wrinkles, while a thickness of greater than 5 mm tends to reduce the flexibility and tends to produce an uncomfortable feeling upon attachment, while also tending to cause more physical irritation.

The main component of the adhesive layer 2 is a pressure-sensitive adhesive. The structural material is not particularly restricted but is preferably one with adhesive strength sufficient to fix a drug onto the surface of the skin for long periods at ordinary temperature, and for example, there may be mentioned acrylic-based adhesives, rubber-based adhesives and silicone-based adhesives. Rubber-based adhesives are preferred for use among these from the standpoint of their satisfactory adhesive properties and drug release properties, and particularly preferred for use are natural rubber, synthetic isoprene rubber, polyisobutylene, polyphenyl ether, polyurethane, polyisoprene, polybutadiene, styrene-butadiene copolymer, styrene-isoprene copolymer, styrene-isoprene-styrene block (SIS) copolymer and the like. When a SIS copolymer is used, SIS bases by Shell Chemical Co., Ltd. (trade names: CALIFLEX Tr-1107, CALIFLEX TR-1111, CALIFLEX TR-1112 and CALIFLEX TR-1117), SIS bases by JSR Co., Ltd. (trade names: JSR5000, JSR5002 and JSR5100) and SIS bases by Zeon Corp. (trade name: QUINTAC 3570C) and the like are most preferred.

If necessary, an additive such as a tackifier, softening agent, filler, antioxidant, absorption accelerator or the like may be added to the adhesive layer 2. Such additives include, for example, tackifiers such as alicyclic saturated hydrocarbon resins (trade name: ARKON P-100, etc. by Arakawa Chemical Industries, Ltd.), rosin esters (trade names: KE-311, KE-100, etc. by Arakawa Chemical Industries, Ltd.), hydrogenated rosin esters (trade names: FORAL 105, FORAL 85, etc. by Hercules Co., Ltd.), hydrogenated alicyclic hydrocarbons (trade name: ESCOREZ 5300, etc. by Exxon Chemical Co., Ltd.), polyterpene resins, petroleum resins and phenol resins; softening agents such as a liquid paraffin, polybutene, liquid polyisobutylene and animal and vegetable oils; as well as fillers, antioxidants and the like. If necessary, an absorption accelerator may be added to the pressure-sensitive adhesive for improved skin penetration of the drug, and as examples of such absorption accelerators there may be mentioned isopropyl myristate, diethyl sebacate, sorbitan monolaurate, sodium oleyl phosphate, sodium lauryl sulfate, octylphenyl ether, lauryl ether, lauroyl diethanolamide, lauroyl sarcosine, oleyl sarcosine sugar ester, lecithin, glycyrrhizin, urea, salicylic acid, calcium thioglycolate, lactic acid, lactic acid esters, olive oil, squalene, lanolin, liquid paraffin and glycerin. In addition, pigments, aromatics, ultraviolet absorbers, surfactants, pH adjustors and the like may also be added to the pressure-sensitive adhesive as appropriate depending on the purpose of the patch.

When a drug is to be held in a patch according to this embodiment, it may be simply combined with the pressure-sensitive adhesive. As examples of such drugs there may be mentioned general anesthetics, hypnotics, analgesics, antipyretic/antiphlogistic analgesics, steroid hormones, analeptic/psychostimulants, psychoneurotic agents, local anesthetics, myorelaxants, autonomic agents, anti-allergic agents, anti-histamines, cardiac stimulants, antiarrhythmic agents, diuretics, antihypertensive agents, vasoconstrictors, vasodilators, calcium antagonists, antimicrobial agents, agents for parasitic skin conditions, skin softeners, antibiotics, antidotes, antitussive agents, antipruritic agents, soporifics, psychoactive agents, antiasthmatic agents, hormone secretion promoters, antiulcer agents, anticancer agents, vitamins, and the like.

The thickness (coating thickness) of the adhesive layer is preferably 10 μm to 400 μm. If the thickness of the adhesive layer 2 is greater than 400 μm, the drug in the pressure-sensitive adhesive tends to have poor release properties, and if it is less than 10 μm the adhesion onto skin is reduced, tending to result in peeling.

The patch body 3 comprising the support 1 and the adhesive layer 2 is preferably cut with rounded corners. Once part of the patch turns up and peels off, the horny skin layer and dust adhere to that section, making reattachment difficult. Particularly in cases where the patch has a rectangular shape, the corners tend to get caught on clothing, etc., and are the first to turn up and peel off. The patch therefore preferably has rounded corners that are less prone to being caught on clothing and the like, thereby further preventing occurrence of peeling. When the corners of the patch body 3 are rounded, the roundness preferably has a curvature radius of 5 mm or greater. A radius of less than 5 mm tends to insufficiently reduce peeling.

As shown in FIG. 1, the release film 4 has a wave-shaped slit 42 at the approximate center, extending from one edge toward the opposite edge. The height of the slit 42 (height R in FIG. 4) is preferably 4 mm to 8 mm, and more preferably 6 mm to 7 mm. The wave pitch of the slit 42 (length P in FIG. 4) is 6 mm to 12.5 mm. The reason for this wave height and wave pitch of the slit 42 is to improve the handleability, as will explained below.

The release film 4 is released during use, being attached to the entire surface of the adhesive layer 2 in a releasable manner, and when it is attached to the entire surface of the adhesive layer 2 in a releasable manner prior to using the patch body 3, an effect is provided of preventing wrinkles in the highly flexible and elastic patch body 3 and preventing escape of the drug component or moisture in the adhesive layer 2. There are no particular restrictions on the structural material of the release film 4, and it may be appropriately selected from among resin films of polyethylene terephthalate, etc., paper and the like having a thickness of about 50 μm after release treatment. The release film 4 preferably has appropriate rigidity. The reason for this, as will be explained below, is for improved handleability of the release film 4 for the release procedure, and more satisfactory attachment.

Figure 3:
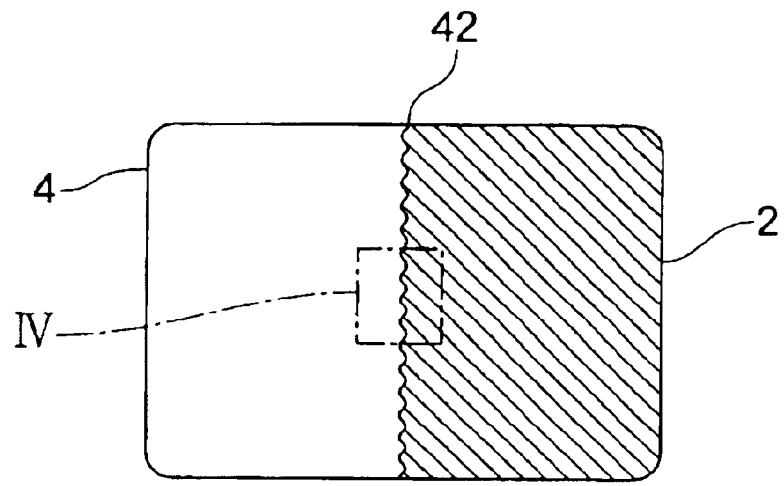
FIG. 3 is a plan view showing the state of the patch of FIG. 1 after half of the release film has been peeled off.

Attachment of a patch having such a construction onto the skin S of an affected area as the attachment site will now be explained with reference to FIGS. 3 to 5.

Figure 7:
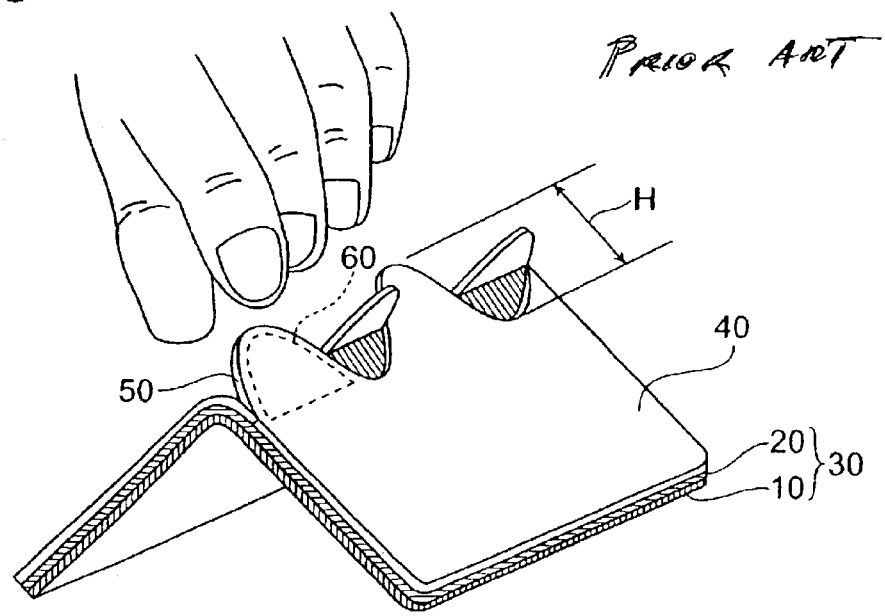
FIG. 7 is a perspective view showing the state of a conventional patch when bent.

First, when the patch is slightly bent along the slit 42 of the release film 4, the edge of the release film 4 along the slit 42 separates from the adhesive layer 2 because of the wave shape of the slit 42 of the release film 4, similar to the case of the conventional patch shown in FIG. 7. Next, a portion of the separated edge, i.e. the grip section 44 of the release film 4 shown in FIG. 4, is gripped with the fingers, and one half of the release film 4 split by the slit 42 is peeled off, thus exposing the surface of the adhesive layer 2 to produce the state shown in FIG. 3. The exposed surface of the adhesive layer 2 is then attached to the attachment site on the affected area of the skin S.

Next, as shown in FIG. 5, the other edge of the release film of the patch which has not yet been peeled off is gripped with the fingers, and the patch is bent slightly toward the opposite edge whereby the release film 4 is pulled away, so that the edge along the slit 42 of the remaining release film separates from the adhesive layer 2 while promptly protruding out from between the attachment site, i.e. the affected area of the skin S shown in FIG. 5, and the adhesive layer 2.

The grip section 44 of the slit 42, which is part of the edge along the slit 42 of the remaining release film 4, is gripped with the fingers.

Finally, the protruding edge of the slit 42 of the remaining release film 4 is slid along the surface of the affected area of the skin S, and the grip section 44 of the slit 42 which has been gripped with the fingers is pulled, whereby it is gradually peeled away, to allow the remaining section of the patch to be satisfactorily attached to the affected area of the skin S without wrinkles.

The efficacy of the patch of this embodiment which allows such a smooth attachment procedure will now be explained in detail in comparison with a conventional patch.

Figure 8A:
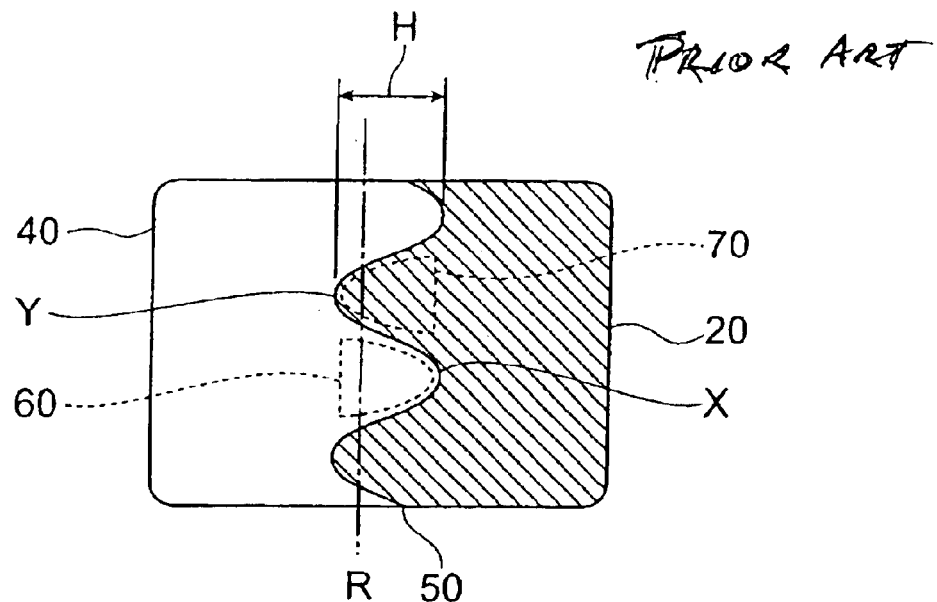
FIG. 8A is a front view showing the state of a conventional patch after half of the release film has been peeled off.
Figure 8B:
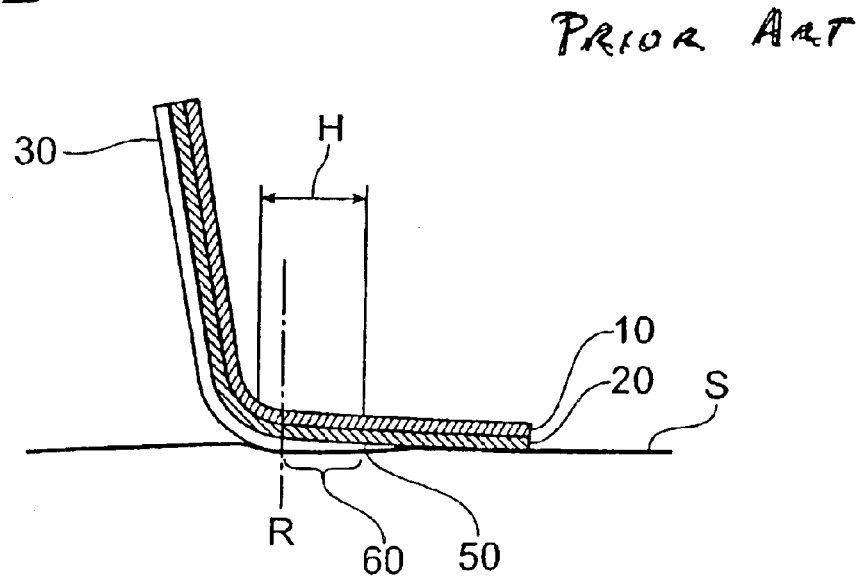
FIG. 8B is a schematic cross-sectional view showing the conventional patch after it has been attached to an affected area of skin in the state shown in FIG. 8A, and then bent.

When, after peeling off one half of the release film 4 in this manner and attaching the exposed surface of the adhesive layer 2 to the affected area of the skin S, the entire adhesive layer is attached while peeling off the remaining half of the release film, since the height H of the wave-shaped slit 50 according to the prior art has been about the size of the fingertip, or a height of about 15 mm±2 mm as shown in FIG. 8B, the grip section of the release film 40 is easy to grip with the finger; however, when the adhesive layer 20 of the patch is attached to the affected area of the skin S and the remaining release film is peeled off, the grip section 60 often becomes caught between the skin S and the adhesive layer 20, making it difficult to grip with the fingers.

This occurs because, as shown in FIG. 8A, a high height H of the wave-shaped slit 50 of the release film 40 gives sufficient area for the grip section 60 for release but also increases the area of the release-inhibiting adhesive section 70, and as shown in FIG. 8B, since the support 10 is thin with high flexibility and elasticity, adhesion between the inhibiting adhesive section 70 and the section S increases, such that the bend line R of the support 10 shifts toward the valley Y end instead of the hill X end of the wave-shaped slit.

Figure 4:
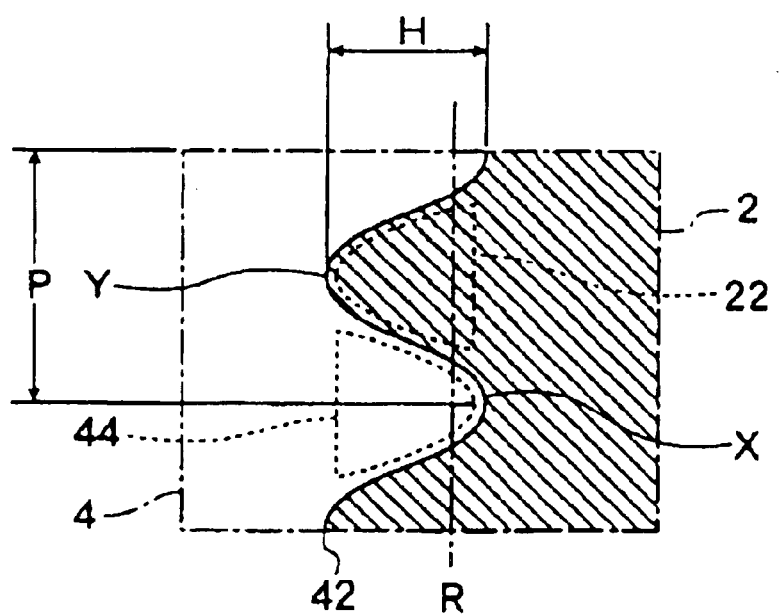
FIG. 4 is an expanded abbreviated plan view of section IV in FIG. 3.

In contrast, the patch of this embodiment has a wave height H of 4 mm to 8 mm for the wave-shaped slit 42 provided on a release film 4 having suitable rigidity, which is lower than that of the prior art, while the wave pitch P of the wave-shaped slit 42 is 6 mm to 12.5 mm, and therefore the area of the grip section 44 shown in FIG. 4 is appropriately small so as to maintain easy gripping while also appropriately reducing the area of the adhesive section 22 which inhibits release of the release film. Even when the support 1 is thin and has high flexibility and elasticity, adhesion between the release-inhibiting adhesive section 22 and the skin S is reduced, thus allowing the bend line R of the support 1 to shift toward the hill X end instead of the valley Y end of the wavle-shaped slit.

Figure 5A:
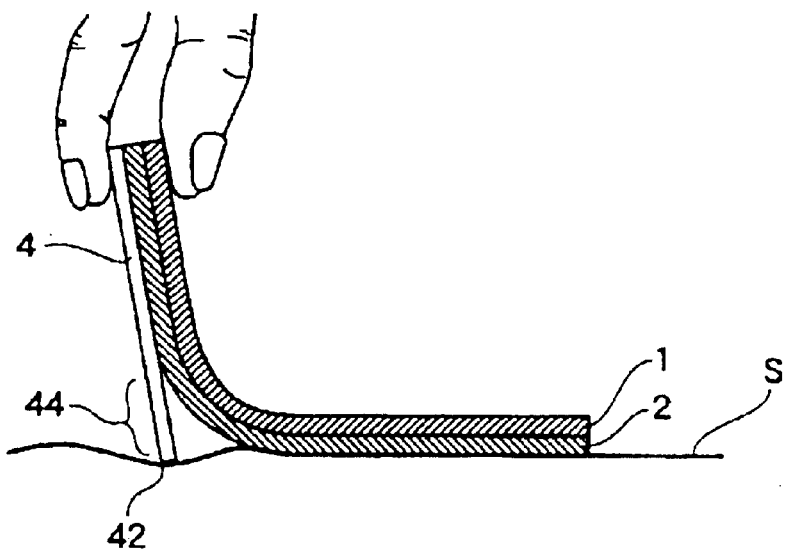
FIG. 5A and FIG. 5B are schematic cross-sectional views of an example of steps for attachment of a patch according to the first embodiment of the invention onto the affected area of skin.
Figure 5B:
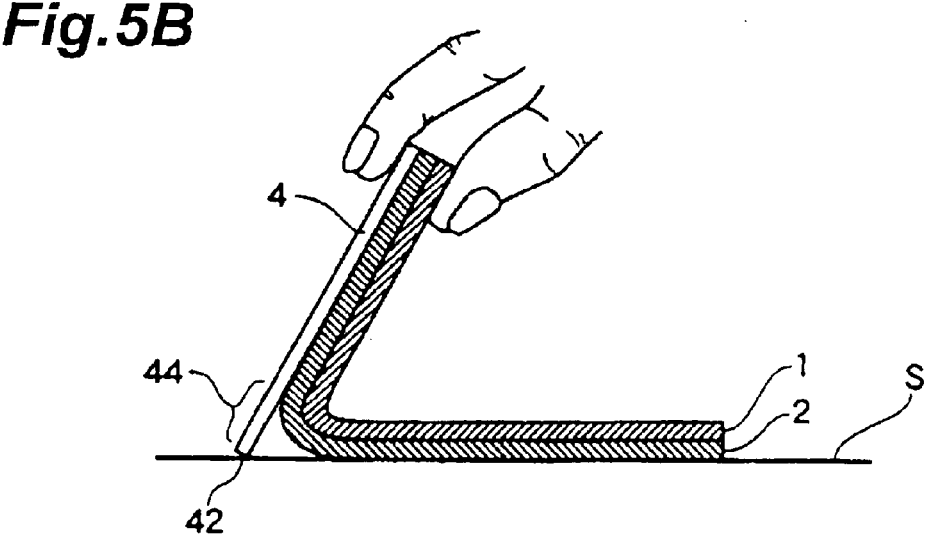

As a result, as shown in FIGS. 5A and 5B, the patch of this embodiment allows the release film 4 to easily protrude outward to be gripped by the fingers without getting caught between the skin S and the adhesive layer 2 during release of the release film, thus preventing the problem illustrated in FIG. 8B, and therefore allows smoother attachment of the patch to affected areas of skin S compared to the prior art.

If the wave height H of the wave-shaped slit 42 provided in the release film 4 is less than 4 mm it becomes difficult to grip with the fingers, while if it is greater than 8 mm it becomes gradually more difficult for the grip section 44 of the release film to flip out from between the skin S and the adhesive layer 2. If the wave pitch P of the wave-shaped slit 42 is less than 6 mm, the grip section 44 of the release film is difficult to grip even when it protrudes out, while if it is greater than 12.5 mm it becomes gradually more difficult for the grip section 44 of the release film to flip out from between the skin S and the adhesive layer 2.

It is effective for the release film 4 on the patch of this embodiment to have appropriate rigidity, in order to give an effect in which the release film easily protrudes out from between the skin S and the adhesive layer 2, as shown in FIG. 5A and in order to allow unwrinkled, satisfactory attachment when attaching the entire adhesive layer to the skin S while peeling off the other half of the release film from the state shown in FIG. 5B, since the patch is gradually attached to the skin S while maintaining sufficient firmness due to the release film.

In addition, the ease of the release procedure of the patch of this embodiment is effective from the standpoint of allowing the adhesive strength of the contact surface between the release film 4 and the adhesive layer 2 to be set to within a wider range than according to the prior art, and of providing the following advantages for storage prior to use or for the production process, which have not existed in the prior art.

Firstly, since release of the release film 4 from the adhesive layer 2 has been difficult according to the prior art, it has been necessary to reduce the adhesive strength to some degree, and this has led to the problem of peeling of the release film 4 before use which exposes the adhesive layer 2 and permits escape of the drug component or moisture in the adhesive layer 2, or the problem of peeling from the skin after attachment; however, the patch of the present invention can adequately prevent such problems since the adhesive strength can be set within a wider range than according to the prior art.

Secondly, when the adhesive strength is increased between the release film 4 and the adhesive surface of the adhesive layer 2 according to the prior art, it has been necessary to subject the release film 4 to special working such as embossing, but with the easier release procedure a smooth film is sufficient. This allows simplification of the production process, while also offering improvement in productivity and lower cost compared to the prior art.

Figure 6:
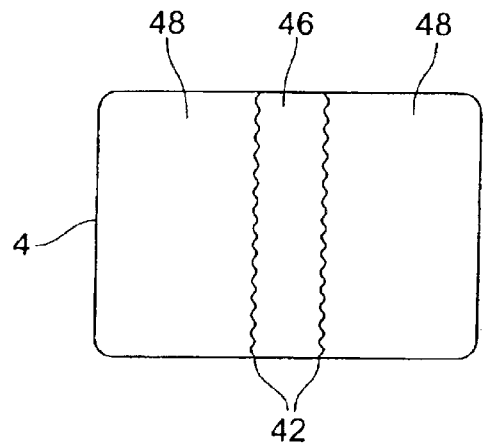
FIG. 6 is a plan view of a second embodiment of the patch of the invention.

The patch of the invention may alternatively have two wave-shaped slits 42 in the release film 4 such as shown in FIG. 6.

When the release film 4 is provided with two wave-shaped slits 42, the positional relationship between the slits 42 is preferably substantially parallel. Here, "substantially parallel" means that where the two wave-shaped slits approximate complete waves, the center line of each wave which bisects the wave amplitude is parallel to the short side of the rough rectangular shape of the release film. When two slits are provided, the slits 42 are preferably formed at a spacing of 20 mm to 30 mm.

Attachment of a patch to an affected area of skin S will now be explained with reference to FIG. 6, for a case where two wave-shaped slits 42 are formed in the release film 4.

First, when the patch is slightly bent along one of the two wave-shaped slits 42 of the release film 4, the edge of the release film 4 along the slit 42 separates from the adhesive layer 2 because of the wave shape of the slit 42 of the release film 4. Next, a portion of the edge of the release film that has separated from the adhesive layer 2, i.e. the grip section 44 shown in FIG. 4, is gripped with the fingers, and the release film 46 between the two slits 42 which is roughly at the center of the release film 4 is peeled off first. The surface of the adhesive layer 2 that has been exposed after peeling off the release film 46 between the two slits 42 is attached to the desired area of the affected area S for provisional affixment of the patch.

Next, as in FIG. 5, the edges of the non-released sections 48 of the release film which are at both ends of the paste area of the patch provisionally affixed to the affected area S are gripped with the fingers, and the patch is bent slightly so that the release film 4 is pulled away, whereby each edge along the slit 42 of the remaining release film separates from the adhesive layer 2 while promptly protruding out from between the attachment site, i.e. the affected area of the skin S shown in FIG. 5, and the adhesive layer 2.

The grip section 44 of each slit 42, which is part of the edge along the slit 42 of the remaining release film 4, is gripped with the fingers.

Finally, the protruding edge of the slit 42 of the remaining release film 4 is slid along the surface of the affected area of the skin S, and the grip section 44 of the slit 42 which has been gripped with the fingers is pulled, so that the end sections 48 of the release film 4 are gradually peeled away either one at a time or both simultaneously, to allow the remaining section of the patch to be satisfactorily attached to the affected area of the skin S without wrinkles.

Providing two wave-shaped slits 42 in the release film 4 is effective from the standpoint of allowing the release film 46 between the slits 42 to be peeled off before attachment so that the exposed adhesive surface 2 can be used as a paste area for provisional attachment onto the affected area. This function permits reattachment so that more precise attachment to the desired site of the affected area can be achieved. Furthermore, since the patch is adequately affixed to the affected area S before the entire patch is attached, it is possible to subsequently attach the remaining end sections 48 of the release film 4 easily while peeling them off, so that the attachment procedure can be carried out more smoothly.

Sufficiently ensuring a spacing of 20 mm to 30 mm between the wave-shaped slits 42 when two wave-shaped slits 42 are provided in the release film 4 is effective as it allows formation of a suitably sized paste area. Sufficiently ensuring such a spacing between the wave-shaped slits 42 will allow the patch to be firmly affixed to the affected area beforehand, so that the patch can maintain adequate firmness established by the paste area to avoid slipping or peeling off of the patch from the affected area when the remaining end sections 48 of the release film are pulled off, such that satisfactory attachment with no wrinkles can be easily accomplished even with one hand.

Here, it should be noted that the efficacy of providing two wave-shaped slits 42 in the release film 4 only functions when the heights of the wave-shaped slits 42 in the release film 4 are smaller than the prior art, within a suitable range. Even if two wave-shaped slits 42 of a size according to the prior art are provided and the release film 46 between the slits is peeled off to use the exposed adhesive layer surface as a paste area for provisional attachment to the affected area of the skin S, the problem of difficulty when peeling the end sections 48 of the release film will still occur. Also, since the adhesive strength between the release film 4 and the adhesive layer 2 cannot be increased as mentioned above, the effect of the present invention whereby a paste area is used for provisional attachment of the patch to the affected area of the skin S, is inadequate.

The aforementioned explanation dealt with a preferred embodiment of the present invention, but this embodiment is of course not intended to restrict the invention. For example, The wave shape of the slit of the release film is not limited to the one used for this embodiment. Specifically, it may be a sawtooth wave or rectangular wave. Likewise, the position of the slit of the release film is not limited to the one used for this embodiment.

In the embodiment described above, the patch was described as a plaster or the like comprising a dry adhesive containing a drug, but the patch of the invention may also contain a moist ointment such as a poultice as the adhesive.

There are no particular restrictions on such moist ointments, but they preferably have adhesive strength capable of fixing drugs onto the surface of the skin for long periods at ordinary temperature and may also contain water, thickeners, humectants, fillers or, depending on the need, crosslinking agents, polymerization agents, dissolving aids, absorption accelerators, drug effect adjuvants, stabilizers, antioxidants, emulsifiers, drug agents and the like.

Preferred thickeners to be used in moist ointments are those that can stably maintain a moisture content of 30–80% and have water retention properties. Specific examples that may be suitably used are water-soluble polymers that include natural polymers which are vegetable-based such as guar gum, locust bean gum, carrageenan, alginic acid, sodium alginate, agar, gum Arabic, tracaganth gum, karaya gum, pectin, starch, etc., microorganic-based such as xanthan gum, acacia gum, etc. and animal-based such as gelatin, collagen, etc.; semi-synthetic polymers which are cellulose-based such as methyl cellulose, ethyl cellulose, hydroxyethyl cellulose, carboxymethylcellulose sodium, etc. and starch-based such as soluble starch, carboxymethyl starch, dialdehyde starch, etc.; and synthetic polymers which are vinyl-based such as polyvinyl alcohol, polyvinylpyrrolidone, polyvinyl methacrylate, etc., acrylic-based such as polyacrylic acid, polysodium acrylate, etc.; as well as polyethylene oxide, methylvinyl ether/maleic anhydride copolymer and the like.

Polyacrylic acid is particularly preferred as a thickener from the standpoint of high gel strength and excellent water retention, and polysodium acrylate with an average polymerization degree of 20,000 to 70,000 is more preferred. With an average polymerization degree of less than 20,000 the thickening effect becomes weaker tending to result in insufficient gel strength, and with an average polymerization degree of greater than 70,000 the thickening effect becomes too strong, tending to reduce the workability.

As humectants to be used in moist ointments there may be mentioned polyhydric alcohols such as glycerin, propylene glycol and sorbitol, and as fillers there may be mentioned kaolin, talc, titanium, bentonite, aluminum silicate, titanium oxide, zinc oxide, aluminum metasilicate, calcium sulfate, calcium phosphate and the like.

In addition, propylene carbonate, crotamiton, 1-menthol, peppermint oil, limonene, diisopropyl adipate and the like may be added as dissolving aids or absorption accelerators and methyl salicylate, glycol salicylate, 1-menthol, thymol, peppermint oil, limonene, nonylic vanillylamide, pepper extract and the like may be added as drug effect adjuvants to a moist ointment for the invention. If necessary, stabilizers, antioxidants, emulsifiers and the like may also be added to a moist ointment for the invention.

Depending on the need, a crosslinking agent or polymerization agent may be added to the moist ointment to reinforce the moist ointment (adhesive) and provide water retention. Such crosslinking agents and polymerization agents may be appropriately selected depending on the type of thickener, etc.

For example, when polyacrylic acid or a polyacrylic acid salt is used as a thickener, there may be suitably used a compound with at least two epoxy groups in the molecule, an inorganic acid salt such as a hydrochloride, sulfate, phosphate or carbonate or an organic acid salt such as a citrate, tartrate, gluconate or stearate of Ca, Mg or Al, a polyvalent metal compound, for example, an oxide such as zinc oxide or silicic anhydride, or a hydroxide such as aluminum hydroxide or magnesium hydroxide. When polyvinyl alcohol is used as a thickener, there may be suitably used adipic acid, thioglycolic acid, epoxy compounds (epichlorhydrin), aldehydes, N-methylol compounds and complexes containing Al, Ti, Zr, Sn, V, Cu, B, Cr and the like. When polyvinylpyrrolidone is used as a thickener, there may be suitably used methylvinyl ester/maleic anhydride copolymer, polyacid compounds or alkali metal salts (of polyacrylic acid, tannic acid or their derivatives). When polyethylene oxide is used as a thickener, there may be suitably used peroxide, polysulfoneazide or the like. When methylvinyl ether/maleic anhydride copolymer is used as a thickener, there may be suitably used polyfunctional hydroxy compounds, polyamine, iodine, gelatin, polyvinylpyrrolidone, iron, silver, lead salts and the like. When gelatin is used as a thickener, there may be suitably used aldehydes such as formaldehyde, glutaraldehyde and dialdehyde starch, diepoxides such as glyoxal and butadiene oxide, diketones such as divinyl ketone, diisocyanates, and the like.

When a drug agent is to be held in a moist ointment layer, the drug agent may be simply be combined with the moist ointment layer. As examples of such drug agents there may be mentioned general anesthetics, hypnotics, analgesics, antipyretic/antiphlogistic analgesics, steroid hormones, analeptic/psychostimulants, psychoneurotic agents, local anesthetics, myorelaxants, autonomic agents, anti-allergic agents, anti-histamines, cardiac stimulants, antiarrhythmic agents, diuretics, antihypertensive agents, vasoconstrictors, vasodilators, calcium antagonists, antimicrobial agents, agents for parasitic skin conditions, skin softeners, antibiotics, antidotes, antitussive agents, antipruritic agents, soporifics, psychoactive agents, antiasthmatic agents, hormone secretion promoters, antiulcer agents, anticancer agents, vitamins and agents with a whitening effect such as skin beautifying components.

The thickness (coating thickness) of the moist ointment layer laminated on the support is preferably 0.1 mm to 3 mm. If the thickness of the moist ointment layer is greater than 3 mm, the drug in the moist ointment tends to have poor release properties, and if it is less than 0.1 mm the adhesion onto skin is reduced, tending to result in peeling.

The thickness including the support and the moist ointment layer (poultice thickness) is preferably 0.5 mm to 5 mm. If the poultice thickness is greater than 5 mm, the poultice tends to get caught on clothing, etc. and peel off when attached, while if it is less than 0.5 mm the poultice tends to lose its support property, leading to misattachment.

The patch of the invention will now be explained in greater detail by way of examples and comparative examples which are not, however, intended to restrict the invention in any way.

EXAMPLE 1

A patch such as shown in FIG. 1 and FIG. 2 was fabricated in a manner equivalent to the patch (7 cm×10 cm) sold by Hisamitsu Pharmaceutical Co., Inc. under the trade name "LA SALONPAS" but with the following conditions. Number of wave-shaped slits in release film: 1, wave height of wave-shaped slit: 4 mm, wave pitch of wave-shaped slit: 12.5 mm.

EXAMPLE 2

A patch equivalent to the one used in Example 1 was fabricated with the following conditions different from Example 1. Wave height of wave-shaped slit of release film: 5 mm, wave pitch of wave-shaped slit: 6 mm.

EXAMPLE 3

A patch equivalent to the one used in Example 1 was fabricated with the following conditions different from Example 1. Wave height of wave-shaped slit of release film: 6 mm, wave pitch of wave-shaped slit: 8.5 mm.

COMPARATIVE EXAMPLE 1

A patch equivalent to the one used in Example 1 was fabricated with the following conditions different from Example 1. Wave height of wave-shaped slit of release film: 14 mm, wave pitch of wave-shaped slit: 36 mm. This sample corresponds to a prior art product.

COMPARATIVE EXAMPLE 2

A patch equivalent to the one used in Example 1 was fabricated with the following conditions different from Example 1. Wave height of wave-shaped slit of release film: 5 mm, wave pitch of wave-shaped slit: 20 mm.

COMPARATIVE EXAMPLE 3

A patch equivalent to the one used in Example 1 was fabricated with the following conditions different from Example 1. Wave height of wave-shaped slit of release film: 12 mm, wave pitch of wave-shaped slit: 10 mm.

[Performance Comparison Test]

The patches of Examples 1–3 and Comparative Examples 1–3 above were subjected to a performance comparison test to evaluate the releasing ease of the release films in the following manner.

Five of each of the patches of the examples were prepared. One half of each release film was peeled off, and the patch was smoothly attached to an acrylic board. Next, the other end of the unreleased section of the patch was gripped with the fingers as shown in FIG. 5, the patch was bent thus turning over the release film, and comparison was made based on the average value for the bend angle as measured at the point where the grip section of the slit separated from the adhesive layer.

By comparing the size of the bend angle, it is possible to compare the ease with which the grip section of the slit of the release film protrudes out. A smaller bend angle indicates that the grip section of the slit of the release film more promptly and easily protrudes out without getting caught between the patch body and the acrylic board, which represents the affected area of skin.

Also, by comparing the size of the bend angle at the point where the grip section of the slit of the release film separates from the adhesive layer, it is possible to compare the ease with which the grip section of the slit of the release film can be gripped.

In other words, the smoothness of the attachment procedure can be compared by comparing the "protruding ease" and "gripping ease" of the grip section of the slit of the release film.

The test results for these samples are shown in Table 1 based on the evaluation criteria for the "protruding ease" and "gripping ease" of the grip section of the slit of the release film.

The evaluation criteria for the "protruding ease" of the grip section of the slit of the release film was as follows. 3: Very smooth protrusion of grip section; 2: Smooth protrusion of grip section; 1: Difficult protrusion of grip section.

The evaluation criteria for the "gripping ease" of the grip section of the slit of the release film were as follows. 3: Protruded grip section sufficiently large matching size of fingertips and easy to grip with the fingers; 2: Protruded grip section sufficiently large and easy to grip with fingers; 1: Protruded grip section small and difficult to grip with fingers.

TABLE 1

| | Number of wave-shaped slits | Wave height of wave-shaped slits (/mm) | Wave pitch of wave-shaped slits (/mm) | Bend angle | Protruding ease | Gripping ease |
|---|---|---|---|---|---|---|
| Example 1 | 1 | 4.0 | 12.5 | 85° | 2 | 2 |
| Example 2 | 1 | 5.0 | 6.0 | 85° | 3 | 2 |
| Example 3 | 1 | 6.0 | 8.5 | 85° | 2 | 3 |
| Comp. Ex. 1 | 1 | 14.0 | 36.0 | 150° | 1 | 1 |
| Comp. Ex. 2 | 1 | 5.0 | 20.0 | 110° | 1 | 1 |
| Comp. Ex. 3 | 1 | 12.0 | 10.0 | 120° | 1 | 1 |

The results in Table 1 clearly show that when one half of the release film was peeled from the wave-shaped slit and the exposed surface of the adhesive layer was attached to the affected area of the skin, and the patch was then completely attached to the affected area of skin while peeling off the remaining release film, as shown in FIG. 5, the grip sections of the wave-shaped slits of Examples 1–3 of the invention protruded out with a bend angle of about ½ compared to Comparative Examples 1–3.

In the case of Comparative Examples 1–3, however, the bend line of the patch was toward the valley end instead of the hill end of the wave-shaped slit, as shown in FIG. 8, with the same bend angle as Example 1, and the grip section of the wave-shaped slit got caught between the adhesive layer and the acrylic board and could not protrude out. When the bend angle was further increased while pulling the end of the unattached section of the gripped patch in a direction to peel off the attached section, that is, in the direction of the other edge opposite the edge of the gripped patch, the bend line of the patch shifted from the valley end to the hill end of the wave-shaped slit, so that part of the grip section of the wave-shaped slit of the release film protruded out.

As regards the gripping ease of the grip section of the wave-shaped slit of the release film which protruded upon bending, Examples 1–3 were easy to grip with the fingertips, while Comparative Example 1 was difficult to grip with the fingertips since the size of the protruding grip section was small.

Examples 1–3 were examined in detail to determine the order of the protruding ease of the grip section of the wave-shaped slit during bending of the patch and the gripping ease of the grip section. The results indicated that the protruding ease of the grip section of the wave-shaped slit was satisfactory in Example 1, and more satisfactory in Examples 2 and 3. Also, the gripping ease of the grip section of the wave-shaped slit was satisfactory in Examples 1 and 2, and more satisfactory in Example 3. In other words, of Examples 1–3, the patch of Example 3 allowed the smoothest attachment procedure.

These results confirmed that protrusion of the grip section of the slit is hampered when the wave height of the wave-shaped slit is too high at 14 mm or about the size of the fingertip as in Comparative Examples 1–3, while protrusion of the grip section of the slit is only slightly hampered but difficult to grip when it is less than 4 mm. It was also confirmed that protrusion of the grip section of the slit is hampered when the wave pitch of the wave-shaped slit is greater than 12.5 mm. These numerical ranges vary depending on the use environment, the materials, etc., and may be appropriately changed within a range that does not fall outside of the scope of the invention.

INDUSTRIAL APPLICABILITY

As explained above, the present invention provides a novel patch with a function allowing smooth attachment to affected areas of the skin.

More specifically, it provides a novel patch wherein an appropriate range is set for the height of the wave-shaped slit of the release film to be lower than according to the prior art, in order to give the following advantages.

Firstly, the release procedure for the release film is easier than by the prior art.

Secondly, because the release procedure is easier, the adhesive strength between the release film and the adhesive layer can be increased. Consequently, the release film is a smooth film which requires no special working such as embossing. This aspect allows simplification of the production process, while also offering improvement in productivity and lower cost compared to the prior art. In addition, the easier release procedure also prevents release of the release film before use so that escape of the drug component or moisture in the adhesive layer can be prevented.

Thirdly, providing two wave-shaped slits in the release film permits part of the release film to be used as a paste area, so that this section can be used for provisional attachment of the patch to the desired area of the attachment site. By increasing the reliability of this procedure step it is possible to further increase the smoothness of the attachment procedure.

Fourthly, a wide variety of materials from existing structural materials to new structural materials can be used as the support and adhesive in the patch of the invention, in order to ensure the same flexibility, elasticity and adhesion with skin as the prior art.

What is claimed is:

1. A patch provided with a support, an adhesive layer laminated on one side of said support, and a release film attached in a releasable manner to said adhesive layer and having a slit running from one edge to the opposite edge, the patch being characterized in that the shape of the slit in said release film is a wave shape such that, by simply bending said support slightly along said slit while the exposed side of said adhesive layer which has been exposed by peeling off part of said release film along said slit is attached to the attachment site, the edge of said slit of the remaining release film can promptly protrude outward from between the attachment site and said adhesive layer, the wave pitch of said wave-shaped slit of said release film is 6 mm to 12.5 mm, and the wave height of each said wave-shaped slit of said release film is 4 mm to 8 mm.

2. The patch according to claim 1, wherein two said wave-shaped slits are provided in said release film, and the two said slits are substantially parallel to each other.

3. The patch according to claim 2, wherein the spacing between the two wave-shaped slits of said release film is 20 mm to 30 mm.

4. The patch according to claim 1, wherein the wave height of said wave-shaped slit of said release film is 6 mm to 7 mm.

5. The patch according to claim 1, wherein said patch has corners, said corners are rounded so as to have a curvature radius of at least 5 mm.

6. The patch according to claim 1, wherein said adhesive layer is from 10 $\mu$m to 400 $\mu$m thick.

7. The patch according to claim 1, wherein said support is from 0.01 to 5 mm thick.

8. The patch according to claim 1, wherein the spacing between the two wave-shaped slits of said release film is 20 mm to 30 mm, the wave height of said wave-shaped slit of said release film is 6 mm to 7 mm, said patch has corners, said corners are rounded so as to have a curvature radius of at least 5 mm, said adhesive layer is from 10 $\mu$m to 400 $\mu$m thick, and said support is from 0.01 to 5 mm thick.

* * * * *